United States Patent [19]

Butoi

[11] 4,109,132

[45] Aug. 22, 1978

[54] AUTOMATIC WELDING MASK SHUTTER LENS SYSTEM

[76] Inventor: Aristotel Butoi, 689 Seneca Ave., Ridgewood, N.Y. 11227

[21] Appl. No.: 770,638

[22] Filed: Feb. 22, 1977

[51] Int. Cl.² .............................................. B23K 9/32
[52] U.S. Cl. .......................................... 219/147; 2/8
[58] Field of Search ................. 219/147; 2/8; 292/74; 49/386; 335/183; 323/43.5 R

[56] References Cited

U.S. PATENT DOCUMENTS

| | | | |
|---|---|---|---|
| 2,029,977 | 2/1936 | Anderson | 292/74 |
| 2,678,369 | 5/1954 | Van Hook | 219/147 |
| 3,432,967 | 3/1969 | Simon | 292/74 |
| 3,452,253 | 6/1969 | Seidlitz | 335/183 |
| 3,792,226 | 2/1974 | Bush | 219/147 |
| 3,855,521 | 12/1974 | Kiuchi | 323/43.5 R |

FOREIGN PATENT DOCUMENTS

| | | | |
|---|---|---|---|
| 394,751 | 4/1924 | Fed. Rep. of Germany | 219/147 |
| 1,115,861 | 12/1960 | Fed. Rep. of Germany | 219/147 |

*Primary Examiner*—E. A. Goldberg
*Attorney, Agent, or Firm*—Richard L. Miller

[57] ABSTRACT

A system for selectively pivoting a welding mask shutter lens either into an opened or closed position so that between welding operation, the work can be observed directly through the lens window opening with the lens pivoted out of the way; the system including an electromagnet for pivoting the lens out the window opening, and wiring from the electromagnet extending to a pushbutton on a handle of a welding rod holder so to conveniently operate a switch in an electrical circuit with the electromagnet for attracting an iron bar formed on the frame of the lens.

1 Claim, 6 Drawing Figures

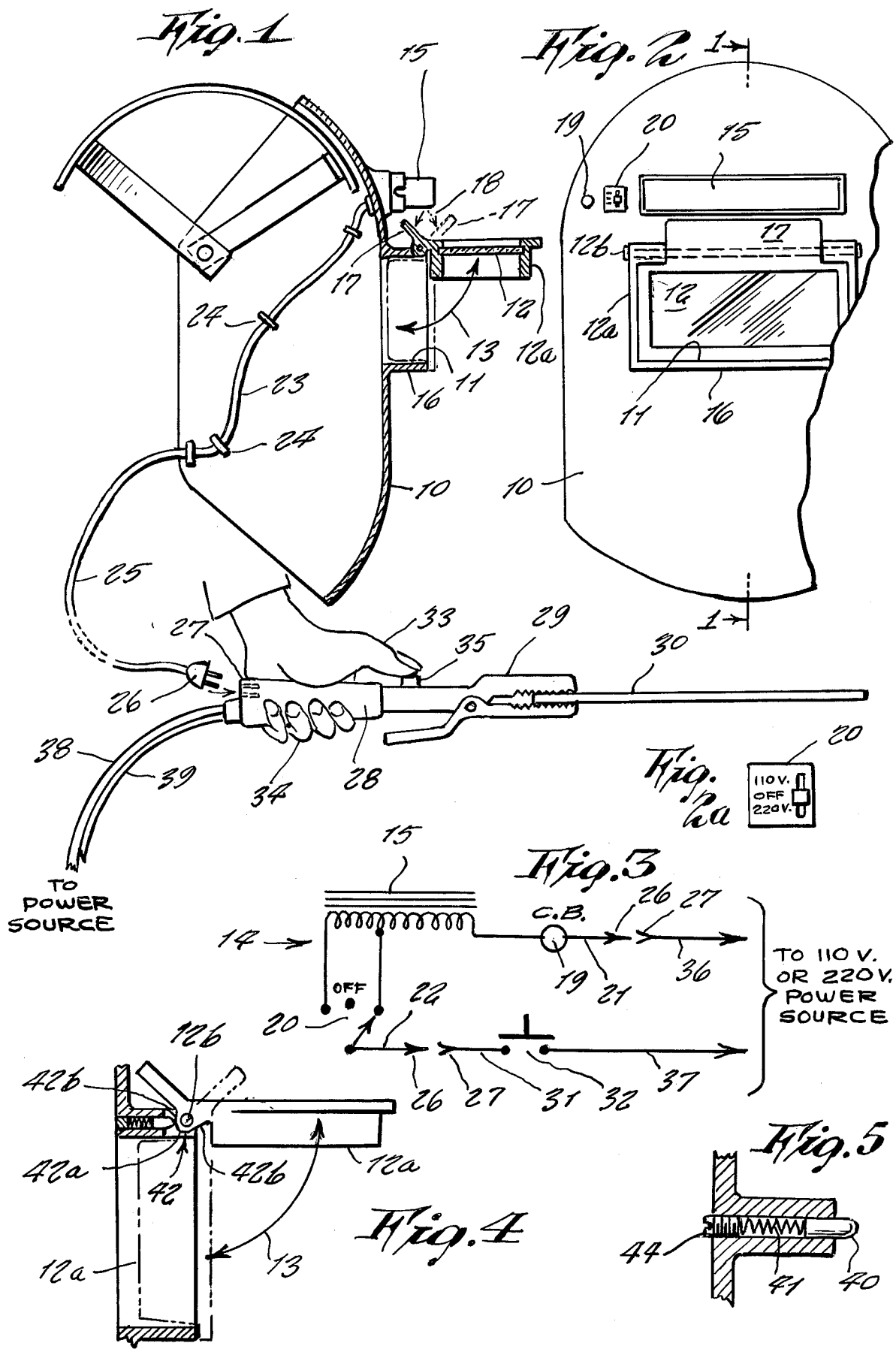

AUTOMATIC WELDING MASK SHUTTER LENS SYSTEM

This invention relates generally to welding equipment.

It is generally well known to those persons who are skilled in the field of welding that a welder occassionally, while performing a weld, likes to observe the progress being made in the work so to know that the weld is being made correctly or properly. It is difficult to see this while the welding is being done because due to the brilliance of the welding light, the welding process is observed through a strongly shaded lens on the helmet which blocks out most of the light. Thus in order to see the work directly between periodic welding processes, the welder must put down the electrode or the welding rod holder so to free one of his hands in order to manually flip up the lens out of the window opening, in order that he can look out through the unshaded opening directly at the work. This action to put down one of the tools so to free a hand is time consuming and extra work so that it is objectionable. Accordingly, it is in want of an improvement.

Therefore it is a principal object of the present invention to provide a system whereby a welding helmet-lens is pivoted out the helmet window opening without need to free the hands off a welding rod holder or electrode, thus saving extra work and time.

Another object is to provide a system which is operated by a pushbutton on the welding rod holder handle so that while the handle is being held in the hand, it is only necessary for one of the fingers of the hand to be depressed on the push button so to pivot the lens on to the window opening.

Another object is to provide a system whereby the lens is pivoted back into a closed position in the window opening again without need to free either hand of the welding tools, by simply once more depressing the same push button.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

FIG. 1 is a side cross-section of the present invention on line 1—1 of FIG. 2.

FIG. 2 is a front view thereof.

FIG. 2a is an enlarged view of a switch on the mask.

FIG. 3 is an electric diagram thereof.

FIG. 4 is an enlarged detail of the window structure.

FIG. 5 is an enlarged detail of adjustment mechanism of FIG. 4

Referring now to the drawing in greater detail, there is shown a welding helmet 10 having on its front side a window opening 11 and lens 12 mounted in a lens frame 12a that is pivotable about a pin 12b in and out of the window opening 11 as indicated by arrow 13, so to selectively permit a welder to see either through the lens or else through the window opening alone.

In the present invention an electrical circuit 14 is incorporated which includes an electromagnet 15 mounted on the front of the helmet directly above the window opening frame 16 so to pull an iron bar 17 formed of the lens frame either forwardly or rearwardly between the positions shown in dotted and solid lines in FIGS. 1 and 4 and as indicated by arrows 18. The iron bar 17 comprises a monolithic portion of the lens frame 12a, the bar being along an axis that intersects transversely the pivot pin 12b.

The electromagnet is connected to a circuit breaker 19 and also to a switch 20 both of which are also mounted on a front side of the helmet for convenient operation. The switch is an on-off switch that selectively allows the electromagnet to be powered either by 110 volts or by 220 volts, as needed.

Two wires 21 and 22 leading from the circuit breaker and the switch are enclosed in a sheath 23 secured by staples 24 on an inner side of the helmet, the sheathed wires dangling from a lower end of the helmet so to form a flexible extension cord 25 having a plug 26 on its free end, and which is plugged into a receptacle 27 formed on a handle 28 of a welding rod holder 29 that holds welding rod 30.

One wire 31 from the receptacle is connected to a pushbutton switch 32 located inside handle 28 and which is manually operative by a finger 33 of an operator's hand 34 holding the handle, depressing a pushbutton 35. Wires 36 and 37 connected to the receptacle and the pushbutton switch respectively are enclosed in sheaths 38 and 39 extending from a rear end of the handle 28 for connection to an electric power source of either 110 volts or 220 volts.

FIGS. 4 and 5 of the drawing illustrate a detent pin 40 biased by a compression coil spring 41 so to bear against a cam face 42 on the lens frame 12a, the cam face including a rise 42a between cam face depressions 42b so that the lens frame is pivoted a full distance in either a closed or opened position instead of stopping in between. In addition a set screw 44 is provided so that the bias force of the compression coil spring can be accurately adjusted for proper operation.

It should be noted that the iron bar protrudes at a 17 degree angle on the lens frame so that in either position it is influenced by magnetic attraction from the electromagnet as shown in FIG. 1, by being directed over the included angle of motion travelled by the bar.

In operative use, to lift the lens, the operator simply depresses the pushbutton. To again lower the lens and close the window opening, he again simply depresses the pushbutton.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An automatic welding mask shutter lens system, comprising in combination, a welding helmet having a window opening on a front side thereof, a shutter lens mounted in a lens frame, said frame being pivotable about a pin so to selectively fit in said window opening when said frame is in a vertical position, or extend forwardly outward therefrom when said frame is in a horizontal position, and an electrical system operated by a push button on a welding rod holder for pivoting said lens frame between said vertical and horizontal positions; said electrical system including an iron bar formed on said lens frame and protruding upwardly therefrom at an angle of 17 degrees along an axis passing transversely through said pivot pin, an electromagnet rigidly mounted on said helmet front side and being located above said frame pivot pin, said iron bar being pivotable across a center of a magnetic field space under said electromagnet so that when said frame is vertical, said iron bar is tilted forwardly, and when said frame is horizontal, said iron bar is tilted rearwardly; said electromagnet being in an electric circuit with a switch in a handle of said welding rod holder, and which is operated by said pushbutton, an on-off switch for selective connection to either a 110v. or 220v. power source and a circuit breaker; and a spring-biased detent pin on said helmet bearing against a cam face on said lens frame forcing said frame to travel over a cam rise between a cam notch at each end of said cam, so that said frame travels a full distance of said travel and thereafter is retained in either a fully horizontal or fully vertical position.

* * * * *